United States Patent
Maase et al.

(10) Patent No.: US 7,495,130 B2
(45) Date of Patent: Feb. 24, 2009

(54) METHOD FOR PRODUCING SUBSTITUTED ARYLCARBOXYLIC ACID CHLORIDES

(75) Inventors: Matthias Maase, Speyer (DE); Gerhard Bertlein, Nechargemuend (DE); Holger Ganz, Ludwigshafen (DE); Matthias Dust, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 128 days.

(21) Appl. No.: 10/564,855

(22) PCT Filed: Jul. 14, 2004

(86) PCT No.: PCT/EP2004/007768

§ 371 (c)(1),
(2), (4) Date: Jan. 17, 2006

(87) PCT Pub. No.: WO2005/012219

PCT Pub. Date: Feb. 10, 2005

(65) Prior Publication Data

US 2006/0178530 A1    Aug. 10, 2006

(30) Foreign Application Priority Data

Jul. 17, 2003    (DE) ............................... 103 32 485

(51) Int. Cl.
*C07C 51/58*    (2006.01)
*C07C 63/10*    (2006.01)
(52) U.S. Cl. ...................... 562/840; 562/856
(58) Field of Classification Search ........................ None
See application file for complete search history.

(56) References Cited

U.S. PATENT DOCUMENTS

| 3,187,057 A | | 6/1965 | Peter et al. |
|---|---|---|---|
| 3,691,217 A | | 9/1972 | McCann |
| 4,276,231 A | * | 6/1981 | Bockmann et al. .......... 562/859 |

FOREIGN PATENT DOCUMENTS

| EP | 0 009 205 | 4/1980 |
|---|---|---|
| EP | 0 554 679 | 8/1993 |
| EP | 0 706 987 | 4/1996 |

* cited by examiner

*Primary Examiner*—Daniel M Sullivan
*Assistant Examiner*—Yevegeny Valenrod
(74) *Attorney, Agent, or Firm*—Oblon, Spivak, McClelland, Maier & Neustadt, P.C.

(57) ABSTRACT

A process for preparing mono- or poly-$C_1$-$C_{20}$-alkyl- and/or -halogen-substituted arylcarbonyl chlorides (I), by, in a first stage, reacting a mono- or poly-$C_1$-$C_{20}$-alkyl- and/or -halogen-substituted aromatic (II) with $CCl_4$ in the presence of a Friedel-Crafts catalyst to give the corresponding mono- or poly-$C_1$-$C_{20}$-alkyl- and/or -halogen-substituted trichloromethylated aromatic (III), and, in a second stage, treating the trichloromethylated aromatic (III) with water or a protic acid in the presence of a catalyst to obtain the arylcarbonyl chloride (I).

In a particularly preferred embodiment, the trichloromethylated aromatic (III) is not isolated as an intermediate and is used in the second stage dissolved in the solvent of the first stage.

11 Claims, No Drawings

METHOD FOR PRODUCING SUBSTITUTED ARYLCARBOXYLIC ACID CHLORIDES

This application is a 371 of PCT/EP04/07768 filed on Jul. 14, 2004.

The invention relates to a process for preparing substituted arylcarbonyl chlorides.

2,4,6-Trimethylbenzoyl chloride (TMBC) is an important raw material for preparing photoinitiators of the acylphosphine oxide type, for example TPO (trimethylbenzoyldiphenylphosphine oxide).

As described in EP-A 0 554 679, TMBC can be prepared in a four-stage synthesis. In this synthesis, mesitylene is reacted in a first stage with chloroacetyl chloride to give chlorotrimethylacetophenone. In a second stage, trichlorotrimethylacetophenone is obtained from chloroacetophenone by reacting with sodium hypochlorite. In a third stage, trichloroacetophenone is reacted with sodium hydroxide solution to give the sodium salt of trimethylbenzoic acid, and trimethylbenzoic acid is obtained from the latter by acidifying with hydrochloric acid. Finally, in a fourth stage, trimethylbenzoyl chloride is obtained from trimethylbenzoic acid by reacting with thionyl chloride.

As a consequence of the multitude of synthetic steps, the synthesis is complicated and characterized by poor yields. In particular, the trimethylbenzoic acid intermediate has to be isolated as a solid and dried before the reaction with thionyl chloride.

In a similar manner, further mono- or polyalkylated benzoyl chlorides can be prepared.

A further method for preparing TMBC is described in EP-A 0 706 987. In this method, mesitylene is carboxylated in the presence of $AlCl_3$ to give trimethylbenzoic acid and the latter is subsequently chlorinated with thionyl chloride to give TMBC. This synthesis too is characterized by poor yields. For instance, the yield of the carboxylation step is only 71%.

It is an object of the invention to provide a simple and economically viable process for preparing substituted benzoyl chlorides, which is characterized especially by improved yields. It is a particular object of the invention to provide a simple and economically viable process for preparing TMBC, which is characterized by improved yields.

This object is achieved by a process for preparing mono- or poly-$C_1$-$C_{20}$-alkyl- and/or -halogen-substituted arylcarbonyl chlorides (I), by, in a first stage, reacting a mono- or poly-$C_1$-$C_{20}$-alkyl- and/or -halogen-substituted aromatic (II) with $CCl_4$ in the presence of a Friedel-Crafts catalyst to give the corresponding mono- or poly-$C_1$-$C_{20}$-alkyl- and/or -halogen-substituted trichloromethylated aromatic (III), and, in a second stage, treating the trichloromethylated aromatic (III) with water or a protic acid in the presence of a catalyst to obtain the arylcarbonyl chloride (I).

Suitable mono- or poly-$C_1$-$C_{20}$-alkyl- and/or -halogen-substituted (F, Cl, Br, I) aromatics, from which the process according to the invention starts, are, for example, benzenes mono- to pentasubstituted by the radicals mentioned, naphthalenes mono- to heptasubstituted by the radicals mentioned, or anthracenes or phenanthrenes mono- to nonasubstituted by the radicals mentioned. When the aromatic is substituted by halogen, it is preferably substituted by chlorine. When it is substituted by alkyl, it is preferably substituted by $C_1$-$C_4$-alkyl.

The process according to the invention preferably starts from mono- to pentasubstituted benzenes of the general formula (IIa).

Preference is thus given to a process for preparing mono- to pentasubstituted benzoyl chlorides of the general formula (Ia)

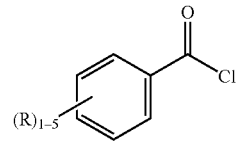

(Ia)

where R is in each case independently halogen (F, Cl, Br, I) or a $C_1$-$C_{20}$-alkyl radical, by, in a first stage, reacting a mono- to pentasubstituted benzene of the general formula (IIa)

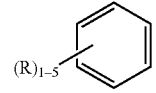

(IIa)

where R is as defined above
with $CCl_4$ in the presence of a Friedel-Crafts catalyst to give the substituted benzotrichloride of the general formula (IIIa)

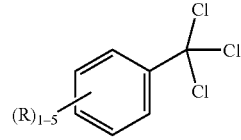

(IIIa)

where R is as defined above,
and, in a second stage, treating the benzotrichloride (IIIa) with water or a protic acid in the presence of a catalyst to obtain the benzoyl chloride (Ia).

The process according to the invention thus replaces the existing four-stage synthesis with a two-stage synthesis which is characterized by a high overall yield.

When the substituted benzene is substituted by halogen, it is preferably substituted by chlorine. When it is substituted by alkyl, it is preferably substituted by $C_1$-$C_4$-alkyl.

The first stage of the process according to the invention preferably starts from a substituted benzene (IIa) which may have 1, 2, 3, 4 or 5 $C_1$-$C_4$-alkyl radicals (i.e. methyl, ethyl, prop-1-yl, prop-2-yl, but-1-yl, but-2-yl, 2-methylprop-1-yl and tert-butyl). The substituted benzene may also have alkyl substituents and halogen substituents (preferably chlorine) simultaneously or be exclusively substituted by halogen. Examples are chlorobenzene, toluene, o-, m- and p-xylene, mesitylene, pseudocumene, hemellitol, ethylbenzene and cumene.

In particular, the process according to the invention is used to prepare 2,4,6-trimethylbenzoyl chloride (Ib) as the substituted aromatic (II) from mesitylene (1,3,5-trimethylbenzene).

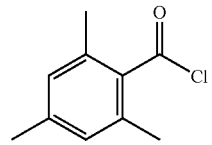

(Ib)

In the first stage, the substituted aromatic (II) is reacted with $CCl_4$ in the presence of a Friedel-Crafts catalyst. Friedel-Crafts catalysts which are suitable for alkylating aromatics with chloroalkanes are known to those skilled in the art. Suitable catalysts are, for example, $AlCl_3$, $FeCl_3$, $AlBr_3$, $CoCl_3$, LiCl, $LiClO_4$, $SnCl_4$, $TiCl_4$, $ZrCl_4$, $SbCl_5$, $CoCl_2$, $BF_3$, $BCl_3$ and $ZnCl_2$, and all Friedel-Crafts catalysts described in George Olah, "Friedel Crafts and related reactions", Vol. 1, 201 and 284-290 (1963). In addition, Brønsted acids may also be used as Friedel-Crafts catalysts. Suitable are, for example, sulfuric acid, phosphoric acid, polyphosphoric acids, pyrosulfuric acid, fluorosulfuric acid, chlorosulfonic acid, methanesulfonic acid, p-toluenesulfonic acid, trifluoroacetic acid and trifluoromethane acid. Preference is given to using $AlCl_3$ as the Friedel-Crafts catalyst in the process according to the invention.

The molar ratio of $CCl_4$ to alkyl aromatic is generally from 1:1 to 15:1, preferably from 1.5:1 to 7:1.

H. Hart and R. Fisch, J. Am. Chem. Soc. (1961), p. 4460-4466 and A. Siciliano, K. Nieforth, J. Med. Chem. (1971), p. 645-646 disclose the performance of the Friedel-Crafts alkylation of alkyl aromatics with $CCl_4$ at a molar ratio of $CCl_4$ to alkyl aromatic of from 4:1 to 13:1. $CCl_4$ is removed from the product after the reaction and appropriately recycled. However, the removal of large amounts of $CCl_4$ is complicated, which is why it is desirable to work with a very small $CCl_4$ excess. In fact, it has been found that, surprisingly, the Friedel-Crafts reaction proceeds with a good yield at a molar ratio of $CCl_4$ to alkyl aromatic of from only 1:1 to 3.5:1, preferably from 1.5:1 to 2:1. Therefore, in one embodiment of the invention, the Friedel-Crafts alkylation of the substituted aromatic (II), preferably of the substituted benzene (IIa), more preferably of mesitylene, is carried out at a molar ratio of $CCl_4$ to aromatic of from 1:1 to 3.5:, preferably from 1.5:1 to 2:1.

Per equivalent of the substituted aromatic (II), preferably of the substituted benzene (IIa), especially mesitylene, generally from 1 to 3, for example approx. 2 equivalents of $AlCl_3$ are used. In one embodiment of the process according to the invention, this ratio (equivalents of $AlCl_3$ to substituted aromatic) is from only 1 to 1.5, in particular from 1 to 1.3, especially from 1.1 to 1.2. It has been found that, when TMBT is prepared from mesitylene, the amount of $AlCl_3$ can be lowered down to a very low excess without the yield of TMBT falling noticeably. This allows the process to be operated more cost-effectively, since less catalyst is required.

The first stage of the process according to the invention is typically carried out in $CCl_4$ as a solvent. However, further solvents may also be present in addition to $CCl_4$. Suitable further solvents are haloalkanes such as dichloromethane, dichloroethane, dibromomethane and bromoform, halogenated aromatics such as chlorobenzene, hydrocarbons such as the isomeric pentanes, hexanes, heptanes, octanes, and also higher hydrocarbons having more than 8 carbon atoms, cyclohexane and hydrocarbon mixtures such as petroleum ether and white spirit. The presence of further solvents is preferred if operation is effected only with a small $AlCl_3$ excess, i.e., for example, the amount of $AlCl_3$, in one embodiment of the process according to the invention, is from only 1 to 1.5 equivalents. In this procedure with a small $AlCl_3$ excess, the presence of further solvents may prevent precipitation of a complex of the trichloromethylated aromatic (III) with $AlCl_3$ or other Lewis acids, for example a $TMBT/AlCl_3$ complex, as a solid. The molar ratio of further solvent to $CCl_4$ may, at the start of the reaction, be from 0.2:1 to 10:1, preferably from 0.5:1 to 3:1.

The first stage of the process according to the invention is typically carried out at a temperature of from 0 to 120° C., preferably from 20 to 60° C. The procedure may be to initially charge the Friedel-Crafts catalyst suspended in $CCl_4$ or in the mixture of $CCl_4$ and the further solvent, and to add the substituted aromatic (II) over a certain period, for example from 0.1 to 10 hours, preferably from 0.5 to 5 hours.

When the Friedel-Crafts alkylation (first stage) is carried out with $AlCl_3$ as a catalyst, the trichloromethylated aromatic (III) is generally obtained as the $AlCl_3$ complex. The Friedel-Crafts alkylation is generally followed by the hydrolysis of this $AlCl_3$ complex. This hydrolysis may typically be carried out with ice or a water/ice mixture, for example, at a temperature of from 0 to 10° C. The hydrolysis may be carried out, for example, batchwise by adding the reaction effluent of the Friedel-Crafts alkylation to ice in a stirred apparatus (stirred tank) operated batchwise.

In one embodiment of the invention, the hydrolysis of the $AlCl_3$ complex is carried with water at a temperature of from 10 to 100° C., preferably from 20 to 100° C., more preferably from 35 to 80° C. It has been found that, surprisingly, the hydrolysis of the $AlCl_3$ complex can also be carried out at higher temperatures of above 20° C. or even above 35° C. without decomposition of the trichloromethylated aromatic (III) to the carboxylic acid taking place.

The performance of the hydrolysis at higher temperatures has a series of advantages. The handling of ice on the industrial scale means a high level of complexity and expense. The performance of the hydrolysis at temperatures below 25° C. still means a high level of complexity and expense, since the cooling with river water is generally no longer sufficient here and apparatus having appropriately high cooling performance (cooling units, brine cooling) is required. When the hydrolysis is carried out at excessively low temperatures, there is the risk that the hydrolysis reaction will cease, start up suddenly on heating and release large amounts of HCl gas which is formed in the hydrolysis, which is difficult to handle on the industrial scale and constitutes a safety problem. It is therefore desirable to carry out the hydrolysis at temperatures above 20° C., preferably above 35° C. The higher reaction rates of the hydrolysis at the high temperatures make possible correspondingly shorter residence times, so that the hydrolysis can be carried out continuously in inexpensive small, continuous apparatus such as a mixer-settler apparatus. The continuous process control also allows better control of the reaction.

In the hydrolysis, an organic and an aqueous phase are obtained. The organic phase comprises the trichloromethylated aromatic (III), in some cases even small amounts of the arylcarbonyl chloride (I), unconverted $CCl_4$ and also, if appropriate, the further solvent or solvents.

The trichloromethylated aromatic (III) may be isolated from the organic phase as an intermediate in pure form, preferably by distillation.

In the second stage of the process according to the invention, the trichloromethylated aromatic (III) is treated with water or an (inorganic or organic) protic acid in the presence of a catalyst to obtain the arylcarbonyl chloride (I). Preference is given to organic protic acids such as carboxylic acids and sulfonic acids, particular preference to carboxylic acids. Typically, these react to give the corresponding acid chloride.

In the second stage, the trichloromethylated aromatic (III) may be used in pure form or in the form of a solution of the trichloromethylated aromatic (III) in $CCl_4$ and, if appropriate, the further solvent as is obtained as the organic phase in the hydrolysis of the $AlCl_3$ complex.

In a preferred embodiment, the solution of the trichloromethylated aromatic (III) in $CCl_4$ and, if appropriate, the further solvent is used. This dispenses with the complicated isolation of the intermediate (III).

It has been found that, surprisingly, the use of the organic phase from the hydrolysis of the $AlCl_3$ complex in the second stage of the process according to the invention is not accompanied by any yield losses.

This procedure is accompanied by a series of advantages. Isolation of the trichloromethylated aromatic (III) from the solution in excess CCl$_4$ and, if appropriate, a further solvent mean additional process cost and inconvenience. Since the organic phase is aqueous after hydrolysis of the AlCl$_3$ complex with excess water and this water is distilled over together with CCl$_4$ as the CCl$_4$/water azeotrope in the course of the distillation off, the distilled-off CCl$_4$ cannot be recycled into the Friedel-Crafts alkylation of the first stage without further drying. The use of the aqueous organic phase from the hydrolysis of the AlCl$_3$ complex in the second stage of the process according to the invention circumvents this problem in an elegant manner, since the water present in the organic phase is consumed in the second stage. In this way, the organic phase is "chemically" dried in the second stage. Subsequently, completely dry CCl$_4$ can be distilled off and recycled into the first stage.

In one embodiment of the process according to the invention, the trichloromethylated aromatic (III) is treated with water, i.e. hydrolyzed, in the second stage. The ratio of water to trichloromethylated aromatic (II) is generally from 0.8:1 to 1.2:1, preferably from 0.9:1 to 1.1:1, especially about 1:1. Suitable catalysts are Lewis acids such as AlCl$_3$, FeCl$_3$, AlBr$_3$, CoCl$_3$, LiCl, LiClO$_4$, SnCl$_4$, TiCl$_4$, ZrCl$_4$, SbCl$_5$, CoCl$_2$, BF$_3$, BCl$_3$ and ZnCl$_2$, and all Friedel-Crafts catalysts described in George Olah, "Friedel Crafts and related reactions", Vol. 1, 201 and 284-290 (1963). In addition, Brønsted acids may also be used as catalysts. Suitable are, for example, sulfuric acid, phosphoric acid, polyphosphoric acids, pyrosulfuric acid, fluorosulfuric acid, chlorosulfonic acid, methanesulfonic acid, p-toluenesulfonic acid, trifluoroacetic acid and trifluoromethane acid. A preferred catalyst is FeCl$_3$. The Lewis acid is generally present in amounts of from 0.05 to 5 mol %, preferably from 0.1 to 3 mol %, based on the trichloromethylated aromatic (III). When the Lewis acid used is FeCl$_3$, it may also added as an aqueous solution, for example as a 30% by weight aqueous solution. The reaction may also be carried out in the absence of an organic solvent. However, it is also possible to work in CCl$_4$ or in the mixture of CCl$_4$ and the further solvent from the first (alkylation) stage of the process according to the invention. The reaction temperature in the hydrolysis (second stage) is generally from 20 to 100° C., preferably from 50 to 75° C. In the case of the preparation of TMBC from TMBT, the temperature in the hydrolysis is generally from 20 to 100° C., preferably from 50 to 75° C.

In a further embodiment, the trichloromethylated aromatic (III) is treated with an organic acid in the presence of a catalyst, i.e. acidolyzed, in the second stage of the process according to the invention. Suitable organic acids are, for example, chloroacetic acid or pivalic acid. In one variant of the process according to the invention, chloroacetic acid is used. This has the additional advantage that chloroacetyl chloride is formed as a coproduct and constituents a product of value. Suitable catalysts are Lewis acids such as AlCl$_3$, FeCl$_3$, AlBr$_3$, CoCl$_3$, LiCl, LiClO$_4$, SnCl$_4$, TiCl$_4$, ZrCl$_4$, SbCl$_5$, CoCl$_2$, BF$_3$, BCl$_3$ and ZnCl$_2$, and all Friedel-Crafts catalysts described in George Olah, "Friedel Crafts and related reactions", Vol. 1, 201 and 284-290 (1963). In addition, Brønsted acids may also be used as catalysts.

Suitable are, for example, sulfuric acid, phosphoric acid, polyphosphoric acids, pyrosulfuric acid, fluorosulfuric acid, chlorosulfonic acid, methanesulfonic acid, p-toluenesulfonic acid, trifluoroacetic acid and trifluoromethane acid. A preferred catalyst is FeCl$_3$. The amount of the Lewis acid is typically from 0.01 to 5 mol %, preferably from 0.1 to 3 mol %, based on the alkylbenzotrichloride (III). The reaction temperature in the acidolysis is generally from 20 to 100° C., preferably from 50 to 75° C. In the preparation of TMBC from TMBT, the reaction temperature is generally from 20 to 100° C., preferably from 50 to 75° C.

The alkylbenzoyl chloride (I) may be obtained in pure form by distillation from the organic phase obtained in the hydrolysis or acidolysis.

The process according to the invention replaces the existing four-stage synthesis with a two-stage synthesis. The overall yield over both stages including the workup may, based on substituted aromatics (II) used, be >80%, preferably >85% and even up to 90%. In the preparation of TMBC, for example, an overall yield of 91% is achieved, compared with 81.7% by the existing four-stage synthesis.

The invention is illustrated in detail by the examples which follow.

EXAMPLES

Example 1

Preparation of TMBT 183.3 g (1.375 mol; 1.1 equivalents) of AlCl$_3$ are suspended at 40° C. in 1153.5 g (7.5 mol) of CCl$_4$. Within 83 min, 150 g (1.25 mol) of mesitylene are added dropwise at 40° C. Even after the first drops, the mixture becomes dark red and HCl evolution can be observed. After 90% of the mesitylene has been added, a solid precipitates out. The suspension can be stirred efficiently. On completion of mesitylene addition, the mixture is stirred at 40° C. for a further 90 min. The reaction mixture is poured onto 1500 g of ice/185 g of concentrated HCl, and hydrolyzed. The reaction mixture is added in such a way that the temperature does not rise above 3° C. The aqueous upper phase is discarded. The organic lower phase is dried over magnesium sulfate (washed with CCl$_4$) and distilled. For distillation, 1705.6 g of organic phase are used. At atmospheric pressure, 1413.4 g of CCl$_4$ are distilled off at 76° C. Subsequently, 268.2 g of TMBT are distilled at approx. 1.6 mbar and approx. 98° C., and, according to GC analysis, have a purity of 93.7 area %. The TMBT also contains approx. 2.5 area % of TMBC. The isolated yield of TMBT and TMBC is a total of 87.6%.

Example 2

Hydrolysis of TMBT 268.2 g of TMBT (93.7 area % TMBT=1.053 mol+2.5 area % TMBC) from Example 2 are admixed at room temperature with 0.3 g (0.0019 mol) of (anhydrous) FeCl$_3$. A red coloration can be observed. At 60° C., 19.0 g (1.053 mol) of demineralized water are added dropwise in 44 min, in the course of which gas evolution sets in. On completion of addition, the mixture is stirred at 60° C. for another 105 min. To complete the conversion, a further 0.25 g of water is added until, according to GC analysis, there is no longer any TMBT present. The reaction effluent is distilled without column at 1.8 mbar and 72° C. to give 196.4 g of TMBC (96.0 area %). The yield is 95.8%. For further purification, the TMBC is distilled once again through a column to obtain 147.8 g of TMBC having a purity of 99.5 area %. The overall yield of isolated TMBC based on mesitylene is 83.9%.

Example 3

Preparation of TMBT 216.7 g (1.625 mol; 1.3 equivalents) of AlCl$_3$ are suspended at 40° C. in 1153.5 g (7.5 mol) of CCl$_4$. Within 35 min, 150 g (1.25) of mesitylene are added dropwise at 40° C. Even after the first drops, the mixture becomes dark red and HCl evolution can be observed. On completion of mesitylene addition, stirring is continued at 40° C. for a further 90 min. The reaction mixture is poured onto 2000 g of ice/300 g of concentrated HCl and hydrolyzed. The reaction effluent is added in such a way that the temperature does not rise above 3° C. The aqueous upper phase is discarded. The organic lower phase is dried over magnesium sulfate (washed with $CCl_4$) and distilled. At atmospheric pressure, 1331.4 g of $CCl_4$ are distilled off at 78° C. Subsequently, 272.2 g of TMBT are distilled at approx. 1.1 mbar and approx. 106° C. and, according to GC analysis, have a purity of 91.9 area %. The TMBT also contains approx. 4.7 area % of TMBC. The isolated yield of TMBT and TMBC is a total of 89.8%.

Example 4

Acidolysis of TMBT 258.5 g of TMBT (91.9 area % TMBT=1.0 mol; 4.7 area % TMBC) from Example 3 are admixed at room temperature with 0.2 g (0.0013 mol) of (anhydrous) $FeCl_3$. A red coloration can be observed. At 70° C., 95.5 g (1.0 mol) of chloroacetic acid (CAA) are added dropwise within approx. 2 hours, in the course of which gas evolution sets in. On completion of addition, the mixture is stirred at 70° C. for another 60 min. The reaction effluent is distilled. At 180 mbar and 58° C., 105.5 g of chloroacetyl chloride (CAC) are initially distilled off. This fraction consists of 96.4 area % of CAC and of 3.5 area % of TMBC. This corresponds to a CAC yield of 90%. Subsequently, 196 g of TMBC are distilled off at 4.2 mbar and 86° C. The isolated TMBC yield is 99.3%. The overall yield of isolated TMBC based on mesitylene is 89.2%.

Example 5

Preparation of TMBC Without Isolation of TMBT 250.0 g of $AlCl_3$ (1.875 mol; 1.5 equivalents based on mesitylene) are suspended at 24° C. in 288.4 g of $CCl_4$ (1.875 mol; 1.5 equivalents based on mesitylene). Within 40 min, 150 g (1.25 mol) of mesitylene are added dropwise at 24-55° C. Even after the first drops, the mixture becomes dark red and HCl evolution can be observed. After the mesitylene has been added, there is a suspension which can be efficiently stirred and pumped. The mixture is stirred at 43° C. for another 90 min. The reaction mixture is added dropwise over a period of 20 min to a mixture of 685 g of demineralized water and 115 g of concentrated HCl. The hydrolysis is started at room temperature and kept below 45° C. in the further course by cooling. The hydrolysis reaction commences immediately. On completion of addition of the reaction mixture, two liquid phases form. The lower brown organic phase is removed and initially charged again in a glass flask without further treatment. The mixture is heated at 50° C. and 1.0 g of a 30% by weight solution of $FeCl_3$ (0.00188 mol) in water is added. After approx. 5 min, gentle gas evolution sets in. After the temperature has been increased to 60° C., 15 g of demineralized water are added dropwise within 33 min. Overall, a further 4.5 g (0.25 mol) of demineralized water are added dropwise. On completion of addition, the mixture is stirred for a further 60 min. The resulting reaction mixture is then distilled. Initially, excess $CCl_4$ is distilled off at 120 mbar. Subsequently, TMBC is distilled off at 0.25-0.4 mbar and a temperature of 62-68° C. Overall, 208.1 g (1.14 mol) of TMBC are obtained, which corresponds to a yield of 91.2%.

What is claimed is:

1. A process for preparing 3-, 4- or 5-fold-$C_1$-$C_{20}$-alkyl- and/or mono- or poly-halogen-substituted benzoyl chlorides (Ia),

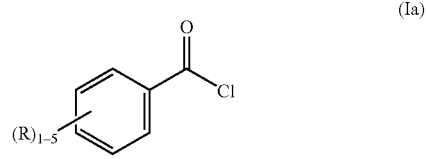

by, in a first stage, reacting a 3-, 4- or 5-fold-$C_1$-$C_{20}$-alkyl- and/or mono- or poly-halogen-substituted benzene (IIa)

with $CCl_4$ in the presence of $AlCl_3$ and subsequent hydrolysis of the formed $AlCl_3$ complex to give the corresponding 3-, 4- or 5-fold-$C_1$-$C_{20}$-alkyl- and/or mono- or poly-halogen-substituted trichloromethylated aromatic (IIIa)

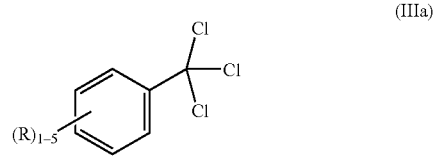

and, in a second stage, the trichloromethylated benzene (IIIa) is hydrolyzed with water in the presence of a catalyst to obtain the benzoyl chloride (Ia), wherein in the second stage the aqueous organic phase from the hydrolysis of the $AlCl_3$ complex is used to hydrolyze the trichloromethylated benzene (IIIa), and water-free $CCl_4$ is distilled off after the second stage hydrolysis.

2. The process according to claim 1, wherein said 3-4- or 5-fold-$C_1$-$C_{20}$-alkyl- and/or mono- or poly-halogen-substituted benzoyl chlorides (Ia) is trimethylbenzoyl chloride of the formula (Ib)

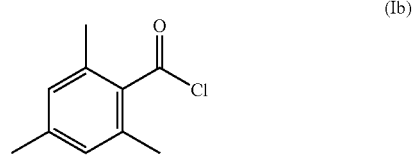

is prepared from mesitylene as the substituted benzene (IIa).

3. The process according to claim 1, wherein the molar ratio of $CCl_4$ to substituted aromatic (IIa) is from 1:1 to 3.5:1.

4. The process according to claim 1, wherein from 1 to 1.5 equivalents of $AlCl_3$ per equivalent of the substituted benzene (IIa) are used.

5. The process according to claim 3, wherein the complex of trichloromethylated benzene (IIIa) and $AlCl_3$ is hydrolyzed with water at from 20 to 100° C.

6. The process according to claim 5, wherein the hydrolysis of the complex of trichloromethylated aromatic (IIIa) and $AlCl_3$ is carried out continuously.

7. The process according to claim 2, wherein the molar ration of $CCl_4$ to substituted aromatic (IIa) is from 1:1 to 3.5:1.

8. The process according to claim 2, wherein from 1 to 1.5 equivalents of $AlCl_3$ per equivalent of the substituted benzene (IIa) are used.

9. The process according to claim 3, wherein from 1 to 1.5 equivalents of $AlCl_3$ per equivalent of the substituted benzene (IIa) are used.

10. The process according to claim 4, wherein the complex of trichloromethylated benzene (IIIa) and $AlCl_3$ is hydrolyzed with water at from 20 to 100° C.

11. The process according to claim 1, wherein the catalyst used in the second stage is $FeCl_3$.

* * * * *